US009078955B2

(12) United States Patent
Shimp

(10) Patent No.: US 9,078,955 B2
(45) Date of Patent: Jul. 14, 2015

(54) COMPOSITES OF HYDROXYAPATITE AND CALCIUM CARBONATE AND RELATED METHODS OF PREPARATION AND USE

(75) Inventor: Lawrence A. Shimp, Burlington, WI (US)

(73) Assignee: CaP Biomaterials, LLC, East Troy, WI (US)

( * ) Notice: Subject to any disclaimer, the term of this patent is extended or adjusted under 35 U.S.C. 154(b) by 0 days.

(21) Appl. No.: 13/317,717

(22) Filed: Oct. 26, 2011

(65) Prior Publication Data

US 2012/0107373 A1 May 3, 2012

Related U.S. Application Data

(60) Provisional application No. 61/406,725, filed on Oct. 26, 2010.

(51) Int. Cl.
*A61L 27/42* (2006.01)
*A61L 27/56* (2006.01)
*C01B 25/32* (2006.01)

(52) U.S. Cl.
CPC ............... *A61L 27/425* (2013.01); *A61L 27/56* (2013.01); *C01B 25/322* (2013.01); *A61L 2430/02* (2013.01)

(58) Field of Classification Search
None
See application file for complete search history.

(56) References Cited

U.S. PATENT DOCUMENTS

| | | | | |
|---|---|---|---|---|
| 4,919,751 | A | 4/1990 | Sumita et al. | |
| 4,976,736 | A | 12/1990 | White et al. | |
| 5,037,639 | A | 8/1991 | Tung | |
| 5,082,808 | A | 1/1992 | Nonami et al. | |
| 5,462,722 | A | 10/1995 | Liu et al. | |
| 5,470,803 | A | 11/1995 | Bonfield et al. | |
| 6,537,589 | B1 | 3/2003 | Chae et al. | |
| 6,582,672 | B1 | 6/2003 | Bonfield et al. | |
| 6,585,946 | B1 | 7/2003 | Bonfield et al. | |
| 7,273,521 | B1 | 9/2007 | Liu | |
| 2004/0250729 | A1 | 12/2004 | Jang et al. | |
| 2006/0110422 | A1 * | 5/2006 | Tas et al. | 424/422 |
| 2007/0041906 | A1 | 2/2007 | Lidgren et al. | |
| 2010/0262258 | A1 | 10/2010 | Gibson et al. | |

FOREIGN PATENT DOCUMENTS

| | | | |
|---|---|---|---|
| GB | 2448489 | A * | 10/2008 |
| WO | 9932401 | A1 | 7/1999 |

OTHER PUBLICATIONS

Gol'dberg et al. "Hydroxyapatite-Calcium Carbonate Ceramic Composite Materials" Inorganic Materials, Nov. 2010, vol. 46, No. 11, pp. 1269-1273.*

Jiang et al. "Improved Mechanical Properties of Nanocrystalline Hydroxyapatite Coating for Dental and Orthopedic Implants" Mater. Res. Soc. Symp. Proc. vol. 1140, 2009, pp. 1-5.*

C. Combes et al. "Calcium carbonate-calcium phosphate mixed cement compositions for bone reconstruction." Journal of Biomedical Materials Research PART A. 2006, vol. 7, No. 2, pp. 318-328.

PCT Search Report from PCT/US2011/001823 issued May 21, 2012.

(Continued)

*Primary Examiner* — Carlos Azpuru
*Assistant Examiner* — Casey Hagopian
(74) *Attorney, Agent, or Firm* — Reinhart Boerner Van Deuren s.c.

(57) ABSTRACT

Carbonated calcium phosphate compositions and methods of preparation, affording enhanced biophysical properties.

7 Claims, 10 Drawing Sheets

(56) References Cited

OTHER PUBLICATIONS

Combes, C.; Rey, C. "Calcium Carbonate Biphasic Cement Concept to Control Cement Resorption" European Cells and Materials, vol. 11, Suppl. 1, 2006 (p. 8).

Ellies, L.G.; Nelson, G.A.; Feathersone J.D.B; "Crystallographic Structure and Surface Morphology of Sintered Carbonated Apatites" Wiley InterScience, Journal of Biomedical Materials Research, Feb. 2, 1988, Abstract; http://www3.interscience.wiley.com/journal/109613966/abstract.

Sampath Kumar T.S.; Manjubala I.; Gunasekaran J. "Synthesis of Carbonated Calcium Phosphate Ceramics Using Microwave Irradiation", ScienceDirect, Biomaterials, vol. 21, Issue 16, Aug. 2000, pp. 1623-1629.

Hirakata, L.M.; Kon, M.; Asaoka K. "1424 Calcium Phosphate Cements Prepared Utilizing Calcium Carbonate Whiskers" Mar. 7, 2002 San Diego Convention Center Exhibit Hall C, http://iadr.confex.com/iadr/2002SanDiego/techprogram/abstract_14933.htm.

Nickel, E.H. "Nomenclature for Mineral Solid Solutions"; American Mingeralogist, vol. 77, pp. 660-662, 1992.

Supplementary European Search Report from European Application No. 11836764.8, issued May 22, 2014, 6 pages.

* cited by examiner

COMPOSITES OF HYDROXYAPATITE AND CALCIUM CARBONATE AND RELATED METHODS OF PREPARATION AND USE

This application claims priority benefit from application Ser. No. 61/406,725 filed Oct. 26, 2010, the entirety of which is incorporated herein by reference.

BACKGROUND OF THE INVENTION

Hydroxyapatite (HA) is considered to be one of the best, if not the best scaffolds for bone growth. However, it is slow to resorb (and has low water solubility), and for that reason there is much interest in alternative materials that resorb faster than HA but still provide good biological properties. One approach is to use alternative calcium phosphates that dissolve more rapidly, such alternative materials including TCP, or mixtures of HA and TCP (biphasic). Another approach that can be used alone or combined with other chemistries is to alter material physical structure to increase the surface area—such as by introducing porosity, and/or by lowering the sintering temperature to reduce density.

Yet other approaches use non-calcium phosphate materials such as calcium sulfate or calcium carbonate. Carbonate-substituted HA is normally found in nature, and the carbonate can replace some of the hydroxide on the calcium hydroxide component and/or substitute some of the phosphate groups with carbonate. This material is very biologically compatible, but is available only as powder because it cannot be sintered to a high density, as sintering above about 825 degrees transforms the carbonate groups to oxide groups. Accordingly, HA and calcium carbonate have been used together as layered materials. One such commercial material has an outer, hydrothermally formed HA layer on a calcium carbonate core. An operative theory is that the HA outer layer provides initial stability and accelerated bone bonding in the graft site, while the calcium carbonate core ensures rapid remodeling once the thin outer layer of HA goes away. Alternatively, calcium sulfate can be used alone as a bone grafting material. However, it is not as osteoconductive as calcium phosphate materials, and—unlike HA—tends to resorb too quickly in many situations. Calcium carbonate can also be used alone as a bone grafting material, but it has many of the disadvantages of calcium sulfate including excessively rapid dissolution.

SUMMARY OF THE INVENTION

In light of the foregoing, it is an object of the present invention to provide various calcium phosphate-related compositions, composites and/or method(s) for their preparation, thereby overcoming various deficiencies and shortcomings of the prior art, including those outlined above. It will be understood by those skilled in the art that one or more aspects of this invention can meet certain objectives, while one or more aspects can meet certain other objectives. Each objective may not apply equally, in all its respects, to every aspect of this invention. As such, the following objects can be viewed in the alternative with respect to any one aspect of this invention.

It can be an object of the present invention to provide various carbonated hydroxyapatite materials compositionally distinct from and heretofore unavailable in the art.

It can also be an object of the present invention to provide such a biocompatible composite/composition with steady remodeling rates, such rates as enhanced by comparison to the prior art.

It can also be an object of the present invention, regardless of any particular composite/composition, to provide a method of preparation such that a resulting material can be sintered without carbonate loss.

It can also be an object of the present invention, alone or in conjunction with one or more of the preceding objectives, to provide dense, non-powder, granular materials useful in a variety of end-use applications, including bone grafting.

Other objects, features, benefits and advantages of the present invention will be apparent from the summary and the following descriptions of certain embodiments, and will be readily apparent to those skilled in the art having knowledge of various biocompatible hydroxyapatite compositions and techniques for their preparation. Such objects, features, benefits and advantages will be apparent from the above as taken into conjunction with the accompanying examples, data, figures and all reasonable inferences to be drawn therefrom, alone or with consideration of the references incorporated herein.

In part, the present invention can be directed to a composition comprising a two-phase composite comprising a matrix phase comprising a sintered calcium phosphate component and a discontinuous phase within such a matrix phase, such a discontinuous phase comprising a plurality of elongated carbonate inclusions. In certain embodiments, such a calcium phosphate component can be selected from sintered hydroxyapatite materials with a Ca/P ratio equal to about or greater than about 1.67. In certain such embodiments, an amount of excess calcium, equal to about 10% to about 25% or more of the total amount of calcium contained in the hydroxyapatite phase can be calcium carbonate. Alternatively, in certain such embodiments, about 15% to about 20% of such a composition can be calcium carbonate. The remainder of any excess calcium not calcium carbonate can be in the form of a non-carbonate salt of calcium such as but not limited to calcium oxide, calcium hydroxide, or a calcium salt other than calcium carbonate.

Regardless, such a composition can have a non-powder, granulate morphology—whether porous or non-porous. In certain such porous embodiments, a pore of such a composition can have a cross-dimension of about 50 microns to about 2000 microns. In certain such embodiments, such a cross-dimension can be about 200 microns to about 600 microns.

In part, the present invention can also be directed to a two-phase composite comprising a hydroxyapatite matrix phase and a discontinuous phase within such a matrix phase, such a composite comprising a Ca/P ratio greater than about 1.67 and such a discontinuous phase comprising a plurality of elongated inclusions comprising a at least a portion of such excess calcium. In certain embodiments, such inclusions of such a discontinuous phase can comprise about 15% to about 20% or more of any such excess calcium component.

Regardless, such inclusions can have a length dimension of about 5 microns to about 20 microns. Without limitation, at least about 90% of such inclusions can have a cross-dimension of less than about 10 microns. Without limitation as to either inclusion length or cross-dimension, such a composite—whether porous or non-porous—can be sintered and/or have a non-powder, granulated morphology.

In part, the present invention can also be directed to a method of preparing a two-phase carbonated hydroxyapatite composition. Such a method can comprise providing a hydroxyapatite material comprising a carbonatable calcium component, such a calcium component providing such a hydroxyapatite material a Ca/P ratio equal to about or greater than about 1.67; sintering such a hydroxyapatite material; and treating such a sintered hydroxyapatite material with a carbon dioxide source to convert at least a portion of such a calcium component thereof to a discontinuous calcium carbonate phase within such a hydroxyapatite phase. In certain embodiments, such a Ca/P ratio can be about 1.67. In certain other embodiments, such a Ca/P ratio can be greater than about 1.67, and such a hydroxyapatite material can comprise an extraneous carbonatable calcium component. Without limitation, such an extraneous component can be selected from calcium oxide, and a calcium oxide precursor selected from calcium hydroxide, calcium carbonate, calcium nitrate, calcium sulfate and calcium salts of organic acids and combinations of calcium oxide and/or calcium oxide precursors.

Without limitation, such a hydroxyapatite material can be sintered at a temperature up to about 1200° C. Optionally, such a material can be partially or less than fully sintered. In certain such embodiments, less sintering can provide more carbonate conversion. Regardless of the extent of sintering, such a carbon dioxide source can be provided in a fluid form. In certain such embodiments, without limitation, such a fluid form can be selected from gaseous and liquid states of carbon dioxide and solutions comprising such a gaseous or liquid state.

In part, the present invention can also be directed to a composition comprising a two-phase calcium phosphate composite characterized by an X-ray diffraction pattern comprising major peaks expressed in degrees two-theta at about 29.5°, about 36.0°, about 39.5°, about 43.0° and about 57.5°, such a composite obtainable by or as be produced by a process comprising sintering a hydroxyapatite material comprising a carbonatable calcium component and carbonating such a sintered material, such a composite comprising the carbonation product of such a calcium component as elongated crystalline inclusions therein.

In certain embodiments, such a composition can have a porous granulated morphology. Without limitation, a pore can have a cross-dimension of about 50 microns to about 2000 microns. In certain such embodiments, a pore can have a cross-dimension of about 200 microns to about 600 microns. Regardless, as can be used to distinguish this and various other embodiments of this invention from powders of the prior art, such granules can have a cross-sectional dimension greater than about 100 microns.

In part, the present invention can also be directed to a method of using elongated carbonate inclusions to affect the strength of a hydroxyapatite material. Such a method can comprise providing a sintered hydroxyapatite material comprising a carbonatable calcium component, with such a component providing such a material a Ca/P ratio equal to about or greater than about 1.67; and contacting such a sintered hydroxyapatite material and a carbon dioxide source, such contact at least partially sufficient to provide elongated carbonate inclusions within such a hydroxyapatite material. As demonstrated herein, such inclusions can affect and/or enhance the strength of such a carbonated hydroxyapatite material versus the strength of an uncarbonated hydroxyapatite material. In certain embodiments, such a carbonated hydroxyapatite material can be sintered at a temperature of about 800° C. Regardless, strength affected by such a method can be gauged by crush test compression and/or particle size data.

DETAILED DESCRIPTION OF CERTAIN EMBODIMENTS

Figure 1A:
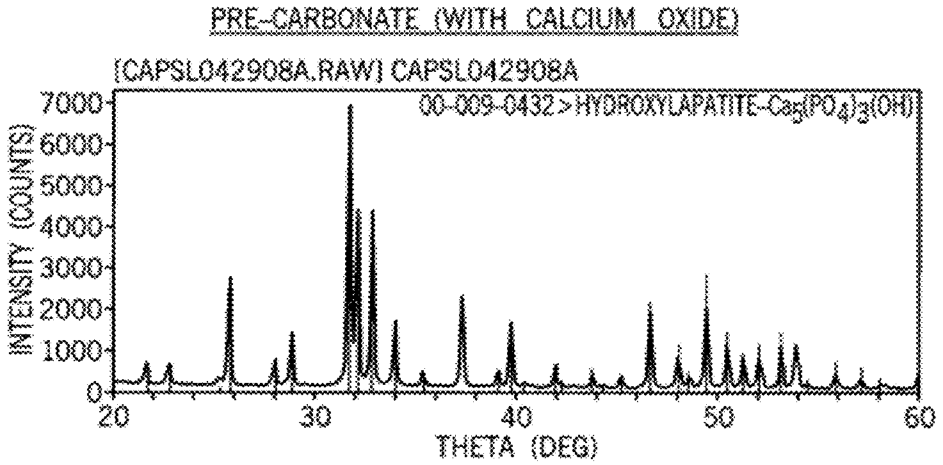
FIGS. 1A-C provide x-ray diffraction spectra on pre- and post-conversion hydroxyapatite, with comparison to calcium oxide and calcium carbonate standards.

With respect to certain non-limiting embodiments, this invention can be considered in the context of a molecular mixture of HA and calcium carbonate. Calcium phosphate and calcium carbonate particles are formed in situ from excess calcium species incorporated into an HA material, producing in an intimate mixture of HA and calcium carbonate that cannot be achieved by mere physical mixing of the two materials. The resulting crystallite size is such that the x-ray diffraction (XRD) pattern shows a crystal pattern for each, and each phase is observable under sufficient magnification, but there is no way to physically separate the component phases. Mixing on this level ensures much greater uniformity than can be obtained through a physical mixing process.

One such HA material of this invention is carbonated after sintering. Only the calcium hydroxide groups are converted (there is no phosphate group substitution), but this still provides many of the chemical features of natural carbonated HA with the added advantage that it can be in a physical form other than powder. For example, it can be made into a porous granulate material (e.g., a particle cross-section dimension greater than about 100 microns) which is very useful in bone grafting applications. (For reference purposes, HA, as compared to tricalcium phosphate (TCP), contains extra calcium in the form of calcium hydroxide to provide a Ca/P ratio of 5/3 (1.67) versus the 3/2 Ca/P ratio of TCP; formula of HA: $Ca_9(PO_4)_6Ca(OH)_2$, formula of TCP: $Ca_9(PO_4)_6$.)

Another embodiment is a material where the amount of calcium in the HA is increased above the Ca/P ratio of HA (i.e., greater than 5/3 or 1.67), and substantially all of the excess calcium is in the form of calcium carbonate. The calcium associated with the HA (within the 5/3 Ca/P ratio) may or may not be in the form of calcium carbonate. Advantages are that the excellent bone biocompatibility of HA is retained, but the remodeling rate is increased due to the presence of the calcium carbonate. Unlike multiple layered materials of the prior art (for example a calcium carbonate material where the outer layer is transformed to HA), the remodeling rate of such a material of this invention is roughly constant because the carbonate is evenly dispersed throughout, which makes for greater predictability. Furthermore, because the material can be fully sintered, it is stronger than many of the lower density (less than fully sintered) forms of HA that are made in an attempt to decrease the remodeling time of HA.

The present invention is not a mere physical mixture of HA and calcium carbonate, as evidenced by an apparent limit as to how much carbonate can be incorporated into such a material. With a physical mixture, there would be no upper limit of carbonate incorporation. However, with respect to certain non-limiting embodiments, about 10% to about 25% of any excess calcium oxide (or another suitable carbonate precursor), representing calcium in excess of a Ca/P ratio of 1.67, can be converted to carbonate. At higher oxide levels, conversion to carbonate may not be complete. Among other related observations, the less an initial HA/calcium oxide/precursor material is sintered the higher the amount of carbonate conversion. Without limitation as to any one theory or mode of operation, carbonate anions are physically larger than oxide ions and have a corresponding spatial requirement within a crystal lattice. It is believed that less sintering correlates to lower material density, and lower density provides more space for physically larger carbonate anions. All such considerations provide further evidence that this invention is not a mere physical mixture but that calcium carbonate is crystallized within and/or incorporated into an HA lattice.

Neutralization of Excess Calcium Oxide or Hydroxide in the Material.

If the conversion to calcium carbonate is not complete and some calcium oxide or hydroxide is left it may be desirable to convert some or all of the excess calcium oxide or hydroxide to a calcium salt. This can be done by reacting an acid (preferably an approximately stoichiometric amount of acid relative to the calcium hydroxide or calcium oxide) with the material. The reaction can be carried out in a water solution, or in the case of a volatile acid such as HCl, the acid can be in the vapor phase to react with the solid calcium oxide or calcium hydroxide containing material.

Description of Calcium Carbonate Materials and Processes.

A process/method of this invention can begin with a material which is made by producing sintered HA with an excess of calcium oxide (or a material capable of being transformed to calcium carbonate such as calcium hydroxide), where the calcium phase (either intrinsic to the HA or additional calcium material, or both) is converted to carbonate by, for example, exposure to $CO_2$ in some form such as a gas, a water solution (carbonic acid) a supercritical fluid, or a compound capable of transferring carbon dioxide. More generally, such a calcium phase can, in the context of this invention, be considered a carbonatable calcium component, capable of being converted to calcium carbonate—such conversion as would be understood by those skilled in the art through use of known techniques, reaction conditions and reagents, including but not limited to those discussed herein.

The process of calcium carbonate formation is generally carried out on sintered HA. Normally, the high temperatures of sintering (if carried out in an oxygen containing atmosphere) transforms most calcium compounds to calcium oxide. Examples of compounds that can be transformed to calcium oxide by heating in an oxygen containing atmosphere are: calcium hydroxide, calcium carbonate, calcium nitrate, calcium sulfate; and calcium salts of organic acids. To facilitate the reaction with carbon dioxide, the calcium oxide can be transformed to calcium hydroxide by exposure to water or water vapor, for example, boiling the material in water.

Producing a Precursor Material.

A preferred process involves addition of extra calcium (for example, calcium oxide or a calcium oxide precursor) to the HA before sintering. The calcium compound can be added to unsintered HA, mixed in by any suitable means, and then the mixture can be sintered. Preferably, the materials to be mixed are powders, and they may be mixed by any suitable means including a grinding/mixing procedure such as ball milling. It is also possible to use a liquid such as water, alcohol, hexane, etc. to facilitate the mixing process. As shown by comparison to the prior art, it is not possible to obtain a molecular mixture of HA and calcium carbonate solely by physical mixing, even if calcium carbonate is used as the calcium compound. Neither calcium carbonate nor HA are completely soluble in any solvent except an acid solution, so (with the exception of an acid solution), at best, the end material is a mixture of particles, and is not mixed at the molecular level. Further, in an acid solution (except for carbonic acid), carbonate decomposes to carbon dioxide gas and calcium hydroxide. However, the process of sintering facilitates the intermingling of the calcium oxide/hydroxide and the calcium phosphate materials to provide more intimate mixing than can be achieved by physical mixing alone. If an acid solution is used (before or in place of sintering), the chemistry is altered, and the material upon drying no longer contains just calcium oxide/carbonate and HA. One useful embodiment of this is to use carbonic acid as the acid source. An approximately stoichiometric amount of carbonic acid can be used to form the carbonated material directly without changing other aspects of the chemistry.

An especially convenient method of making a precursor material is to react phosphoric acid with an excess of calcium hydroxide. One of the common commercial methods of making HA is by reacting phosphoric acid with calcium hydroxide; accordingly, in certain embodiments, this invention can represent a methodology including an excess of calcium hydroxide in the reaction mixture.

Formation of Calcium Carbonate In-Situ.

During sintering, the added calcium precursor remains mixed at the molecular level with the HA, and remains in place during cooling. Preferably, the sintering will be carried out at a temperature sufficient to convert such a calcium compound to calcium oxide. The most direct way to convert the calcium oxide to calcium carbonate in the sintered mixture is to, at a temperature below the approximately 825° C. decomposition temperature of calcium carbonate, expose the sintered material to $CO_2$ gas (either pure or in a gas mixture such as air, nitrogen, water vapor, etc.) until the desired conversion of the calcium oxide to calcium carbonate is achieved. The advantage of this method, as opposed to sintering a reaction mixture containing calcium carbonate and calcium phosphate, is that much higher sintering temperatures can be used, which will result in a stronger, denser material. Hydroxyapatite containing excess calcium, for example, can be sintered at up to about 1200° C., and the excess calcium can then be converted to the carbonate form post sintering; while a calcium carbonate/calcium phosphate mixture can only be sintered to a temperature of about 800° C. while retaining the carbonate phase.

In carrying out the conversion of the sintered material to carbonate, the concentration of $CO_2$ in the treatment gas can be as little as 0.001% or as high as 100%. The $CO_2$ concentration mainly affects the rate of conversion, with higher $CO_2$ concentrations giving a faster conversion. The reaction with carbon dioxide gas can be facilitated by suspending the calcium oxide containing calcium phosphate in water. Another way to facilitate the reaction is to transform the calcium oxide to calcium hydroxide by, for example, boiling the calcium oxide containing material in water, then (optionally) drying it. Solid calcium hydroxide reacts faster with carbon dioxide than solid calcium oxide. Heat can also be used to facilitate the reaction. The temperature should be below the decomposition point of calcium carbonate (which is about 825° C.). Temperatures can be above or below the decomposition point of the precursor material as long as the temperature is below the decomposition temperature of calcium carbonate; for example calcium hydroxide melts at about 580° C. and decomposes at a somewhat higher temperature. This is still below the 825° C. decomposition temperature of calcium carbonate. A reaction carried out at a temperature above the melting point of calcium hydroxide may be useful in providing a denser material than if the reaction were carried out below the melting point.

Water can be used to facilitate the reaction by immersing the solid material to be treated in water, then bubbling the $CO_2$ through the water. While some of the calcium content of the solid material may dissolve in the water and be lost, some will also remain with the solid in a converted form as long as the reaction is not run too long. After the reaction is completed, the solid can be separated from the water by centrifugation, filtration, decantation, etc. In addition to using $CO_2$ gas for carbonate conversion, the $CO_2$ can be in a liquid form, including the form of a supercritical fluid, or a chemical solution capable of causing the conversion (such as carbonic acid, etc.).

The degree of sintering can affect the conversion. Fully sintering the material to a very dense material can make the conversion more difficult: as a molecular mixture, a dense crystal lattice can be considered as having less room for the larger carbonate ions (or even for the hydroxide ions in place of calcium oxide). Therefore, depending on the amount of carbonate desired, it may be necessary to lower the sintering temperature to achieve the full conversion. Alternatively, the lattice density can be decreased by introducing ions known to reduce the density of HA such as magnesium, zinc, manganese, etc.

It is preferred that the mixed material be sintered before the carbonate conversion is carried out, but it is also possible to obtain a molecular mixture without sintering. This can be done, for example, by reacting phosphoric acid with excess calcium oxide or calcium hydroxide (such that a molecular mixture is formed as the phosphoric acid is neutralized), then drying the mixture, and reacting it with carbon dioxide to achieve the conversion to calcium carbonate.

If calcium carbonate is added directly to the phosphoric acid, most likely a post drying $CO_2$ treatment will still be needed because the acid conditions liberate carbon dioxide from calcium carbonate and transform it into the hydroxide. But, if the amount of phosphoric acid is not enough to neutralize all of the calcium carbonate (the final Ca/P ratio is over 3/2) there will be calcium carbonate remaining in the mixture which could be sufficient by itself.

With respect to the present invention, the methods, composites, compositions and/or phases thereof can suitably comprise, consist of or consist essentially of any of the aforementioned components, materials or compounds. Each such component, material and/or compound is compositionally distinguishable, characteristically contrasted and can be practiced in conjunction with the present invention separate and apart from another. Accordingly, it should also be understood that the inventive compositions, composites and/or methods, as illustratively disclosed herein, can be practiced or utilized in the absence of any one component, material and/or compound which may or may not be disclosed, referenced or inferred herein, the absence of which may or may not be specifically disclosed, referenced or inferred herein. Likewise, it should be understood that the inventive compositions, composites and/or methods of this invention can be expressed or claimed providing for any one or more specific components, materials, compounds and/or steps, or by reciting the absence of any one or more specific components, materials, compounds and/or steps.

Whether or not expressly indicated, all numbers expressing component, material and/or compound quantities, concentrations or proportions (e.g., ratios and factors of ratios), dimensions, properties, reaction or process parameters or conditions, and so forth used in the specification and claims are to be understood as being modified in all instances by the term "about". Accordingly, unless indicated to the contrary, the numerical values set forth in the specification and the attached claims are approximations that may vary depending upon the desired properties sought to be obtained by the present invention. At the very least, and not as a limitation of application of the doctrine of equivalents to the scope of such claims, each numerical value should be construed in light of the number of reported significant digits and by applying ordinary rounding techniques.

EXAMPLES OF THE INVENTION

The following non-limiting examples and data illustrate various aspects and features relating to the compositions, composites and/or methods of the present invention, including the preparation of carbonated hydroxyapatite materials, as are available through the synthetic methodologies described herein. In comparison with the prior art, the present methods and compositions/composites provide results and data which are surprising, unexpected and contrary thereto. While the utility of this invention is illustrated through the use of several calcium phosphate compositions/composites and hydroxyapatite and carbonate components thereof, it will be understood by those skilled in the art that comparable results are obtainable with various other compositions/composites and components thereof, as are commensurate with the scope of this invention.

Example 1

Calcium hydroxide (4120 grams) was suspended in 40 liters of water in a 30-gallon plastic tank under continuous agitation. Phosphoric acid, 85% concentration, (3110 grams) was slowly added to the calcium hydroxide. This resulted in about a 21% excess of calcium hydroxide over that needed to make hydroxyapatite. After 24 hours, the reaction mixture was concentrated in a filter press. The filter cake was collected and dried in an oven at 120° C. The dried material was broken into random sized lumps and transferred to alumina crucibles, then sintered at 1100° C. for 4 hours (with an 8-hour heating ramp). After cooling, the sintered material was checked by x-ray diffraction and found to contain about 79% HA and 21% calcium oxide.

Example 2

Some of the material (10 grams) from Example 1 was boiled in (300 ml) water for 3 hours to transform the calcium oxide to calcium hydroxide. The ratio of solids to water was about 1:30. XRD analysis of a sample confirmed the conversion of the calcium oxide to calcium hydroxide.

Example 3

About 50 grams of the boiled material from Example 2 was transferred to boat crucibles and put into a tube furnace. The ends of the tube furnace were sealed except for a ¼ inch hole at the back end and a ¼ inch inlet pipe in the front end. A flow of about 6 cubic ft./hour of $CO_2$ was fed into the furnace through the tube and the furnace was held at 500° C. for 12 hours. XRD analysis of the treated material showed that all of the calcium oxide had transformed to calcium carbonate, while the HA was unchanged.

Example 4

About 10 grams of material from Example 1 was put in a 250 ml gas bubbler jar. It was covered with about 75 ml of water, and stirred with a magnetic stirring bar while $CO_2$ was bubbled through at a rate of about 1 standard cubic foot per hour (SCFH). The reaction ran for 2 hours. The pH was initially about 8.5. At the completion of the reaction the pH was about 6.0. The material was separated from the water by centrifugation, then dried at 90° for 4 hours. XRD analysis showed that the calcium oxide content decreased from 21% to 5%, and the carbonate content was 8%. The supernatant water solution, which was cloudy, was dried and the resulting solid was analyzed by XRD. It was found to be HA with a high proportion of calcium carbonate (about 25%). It was concluded that the conversion reaction converted about half of the calcium oxide in place, but that fragments of the original material broke off during the process (probably from contact with the stirring bar) and became more highly carbonated. Some carbonate may have dissolved during the $CO_2$ treatment and precipitated on carbonated HA powder during the drying process.

Example 5

Calcium hydroxide (4120 grams) was suspended in 40 liters of water in a 30-gallon plastic tank under continuous agitation. Phosphoric acid, 85% concentration, (3110 grams) was slowly added to the calcium hydroxide. This resulted in about a 21% excess of calcium hydroxide over that needed to make hydroxyapatite. After 24 hours, the reaction mixture was concentrated in a filter press. The filter cake was collected and dried transferred to drying pans. The material was placed in a vacuum oven, the air was evacuated, and the oven was backfilled with carbon dioxide and the temperature was raised to 30 degrees C. The material was left in the carbon dioxide atmosphere for 18 hours, then removed and transferred to alumna crucibles. The material was sintered at 800 degrees, and upon XRD analysis it was found that the excess calcium had fully converted to calcium carbonate. The lower sintering temperature is believed to have prevented thermal decomposition of the carbonate material.

Example 6

In accordance with certain non-limiting embodiments of this invention, porous composites and/or compositions can be prepared using techniques known in the art.

Example 6a

A slurry containing calcium phosphate is produced having a molar ratio of calcium to phosphate greater than 1.67. The pH of the calcium phosphate slurry is then reduced to an ideal range of 7 to 4. It can be reduced by adding a buffer or acid; or preferably by converting the calcium oxide (or calcium hydroxide) present in the material to carbonate exposure to carbon dioxide gas. A carbomer and/or polyethylene glycol is then added to the slurry, and allowed to mix for greater than one hour. Once sufficient mixing has taken place hydrogen peroxide is added to the mixture. At this point the mixture can be placed in a heated oven and allowed to dry. Once dry, the material is sintered at a temperature greater than 600 C, but preferably less than 1200 C. The material is then placed in water or a water atmosphere to convert any CaO present to CaOH. Once the CaO is converted the material is placed in a $CO_2$ atmosphere until the desired amount of carbonation is achieved. (If the material is converted to the carbonate form before sintering, and is sintered to a temperature below about 800 C, then the after sintering carbonate conversion step is not necessary.)

Example 6b

A slurry containing calcium phosphate is produced having a molar ratio of calcium to phosphate greater than 1.67. The mixture is then dehydrated to a powder, ideally using a spray dryer. The powder is then mixed with a pore-making material until a homogenous mixture is achieved. (The pore-making material can be an organic material that burns away completely during sintering leaving holes (pores) in its place. Examples include polymer fibers, or even thin (dry) spaghetti rods.) The calcium phosphate/porogen mixture is then pressed to its desired shape at a pressure greater than 1000 psi, but ideally greater than 5000 psi. The pressed piece is than is sintered at a temperature greater than 600 C, but preferably less than 1200 C. Sintering should be done so that the pore making material completely burns out of the material. The material is then placed in water or a water atmosphere to convert any CaO present to CaOH. Once the CaO is converted the material is placed in a $CO_2$ atmosphere until the desired amount of carbonation is achieved.

Example 6c

A slurry containing calcium phosphate is produced to having a molar ratio of calcium to phosphate greater than 1.67. The mixture is than thickened so that the slurry sticks to a polyethylene sponge while still preserving its pores. The sponge is then dried in a heated oven. Once dry the sponge is sintered to greater than 600 C, but preferably less than 1200 C. Sintering should be done so that the sponge completely burns out. The material is then placed in water or a water atmosphere to convert any CaO present to CaOH. Once the CaO is converted the material is placed in a $CO_2$ atmosphere until the desired amount of carbonation is achieved.

Example 6d

Whether or not porous, granulated composites and/or compositions of this invention can be prepared by appropriate grinding and sieving. For instance, porous materials prepared as described in examples 6a-c can be ground to a non-powder granulate of particle cross-dimension greater than about 100 microns.

Example 7

Figure 1B:
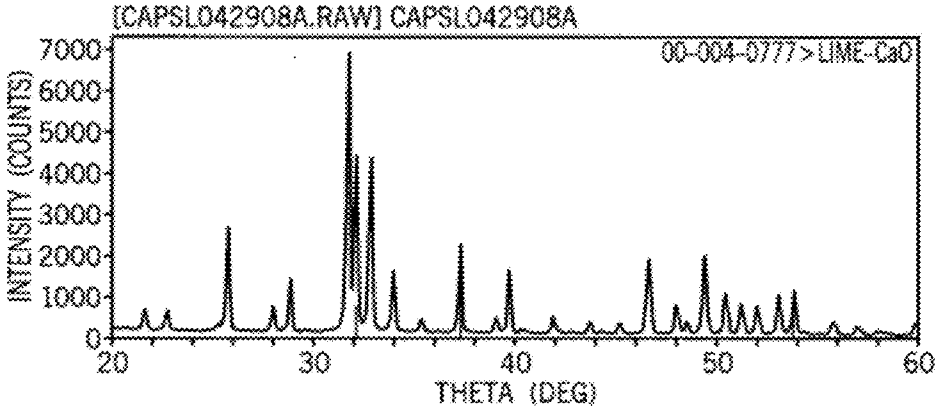
Figure 1C:
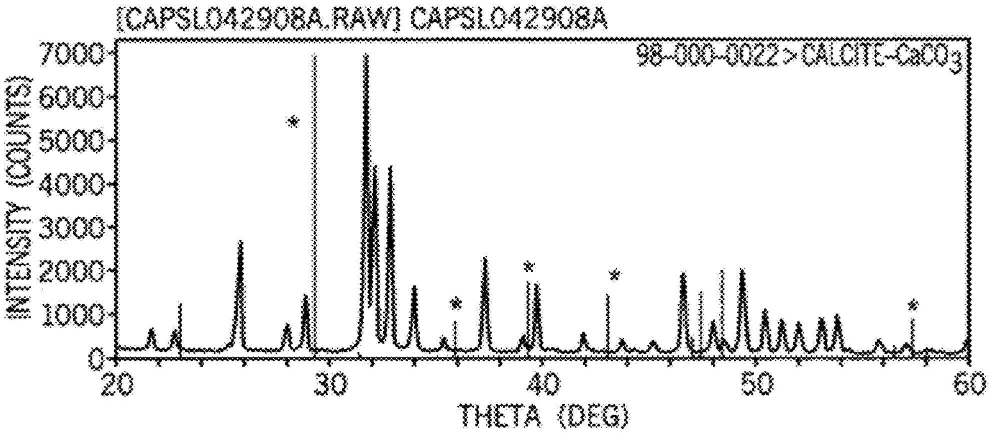

X-ray diffraction (XRD) studies were undertaken on pre- and post-conversion HA, with scans of calcium oxide and calcium carbonate standards provided for purpose of comparison. FIG. 1 provides an XRD pattern for pre-conversion HA. FIG. 1B provides, for comparison purposes, an XRD pattern for calcium oxide. FIG. 1C provides a comparative XRD pattern for calcium carbonate, showing post-conversion carbonate peak positions (*) not present in pre-conversion HA (comparative reference is made to FIG. 1A).

Figure 2A:
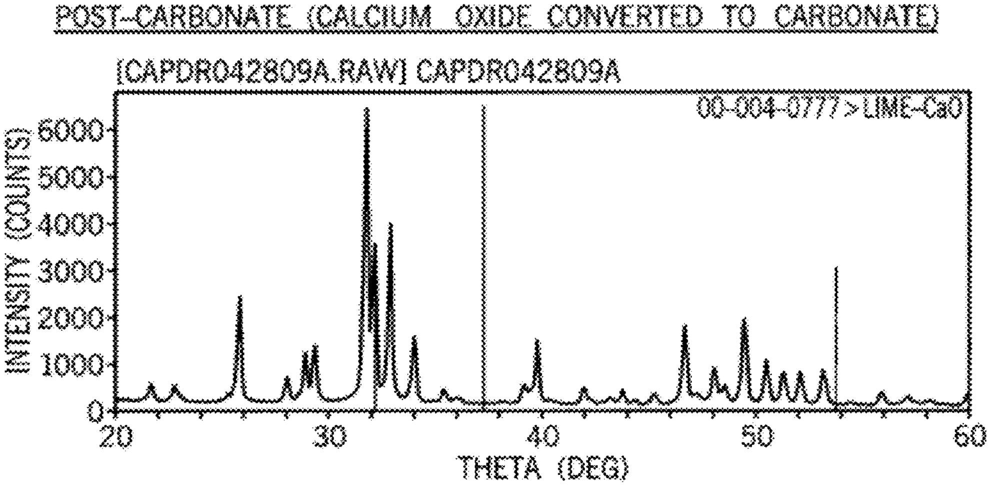
FIGS. 2A-C provide x-ray diffraction spectra for post-conversion hydroxyapatite compositions, in accordance with various non-limiting embodiments of this invention.
Figure 2B:
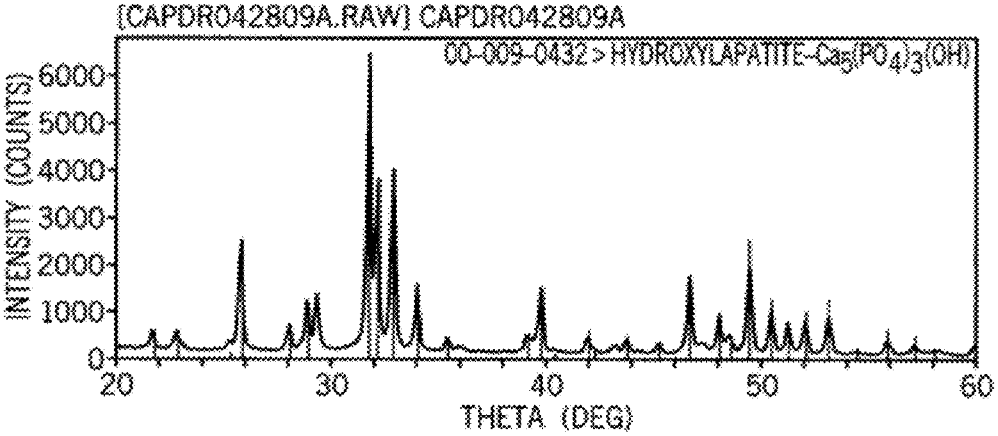
Figure 2C:
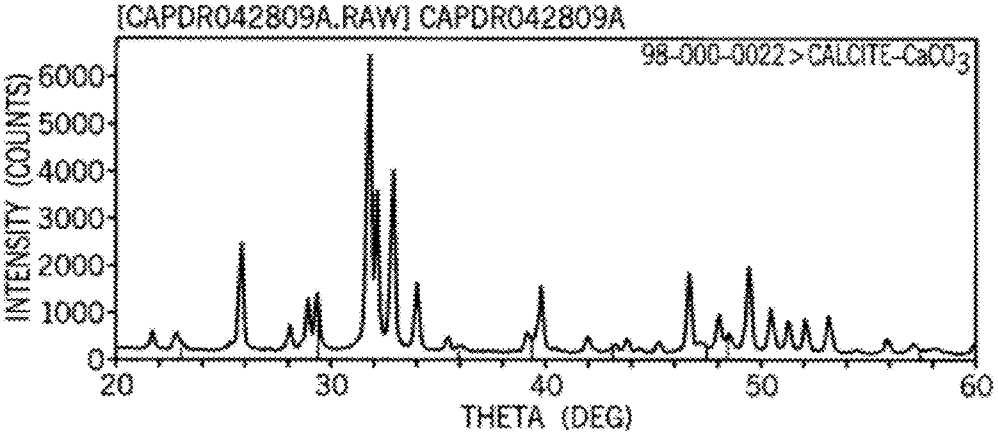

FIG. 2A provides an XRD pattern for post-conversion HA and shows, for comparison, calcium oxide peak positions. FIG. 2B provides an XRD pattern for post-conversion HA and shows, for comparison, peak positions for pre-conversion HA. FIG. 2C provides an XRD pattern for post-conversion HA and shows, for comparison, peak positions attributable to carbonate conversion.

Example 8

Figure 3A:
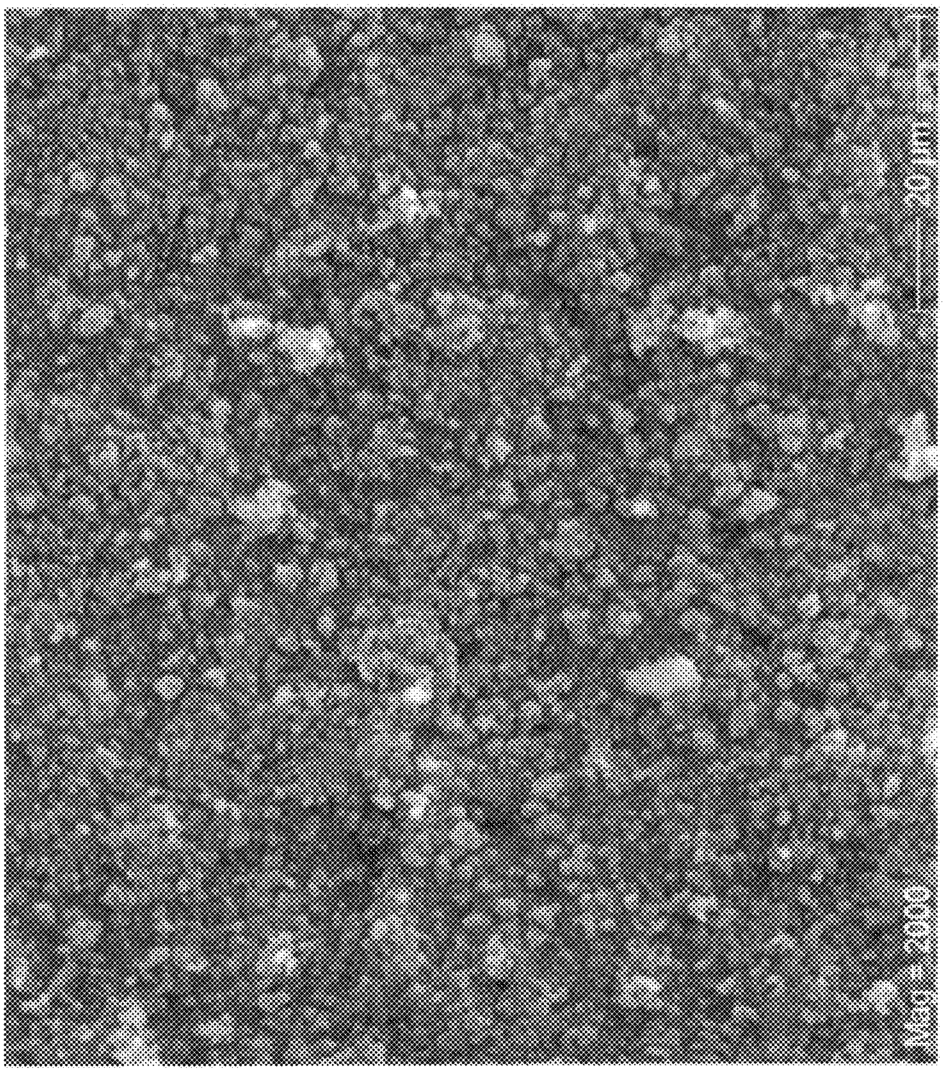
FIGS. 3A-B and 4A-B provide, respectively, scanning electron micrograph images of hydroxyapatite and a non-limiting carbonated hydroxyapatite composite.
Figure 3B:
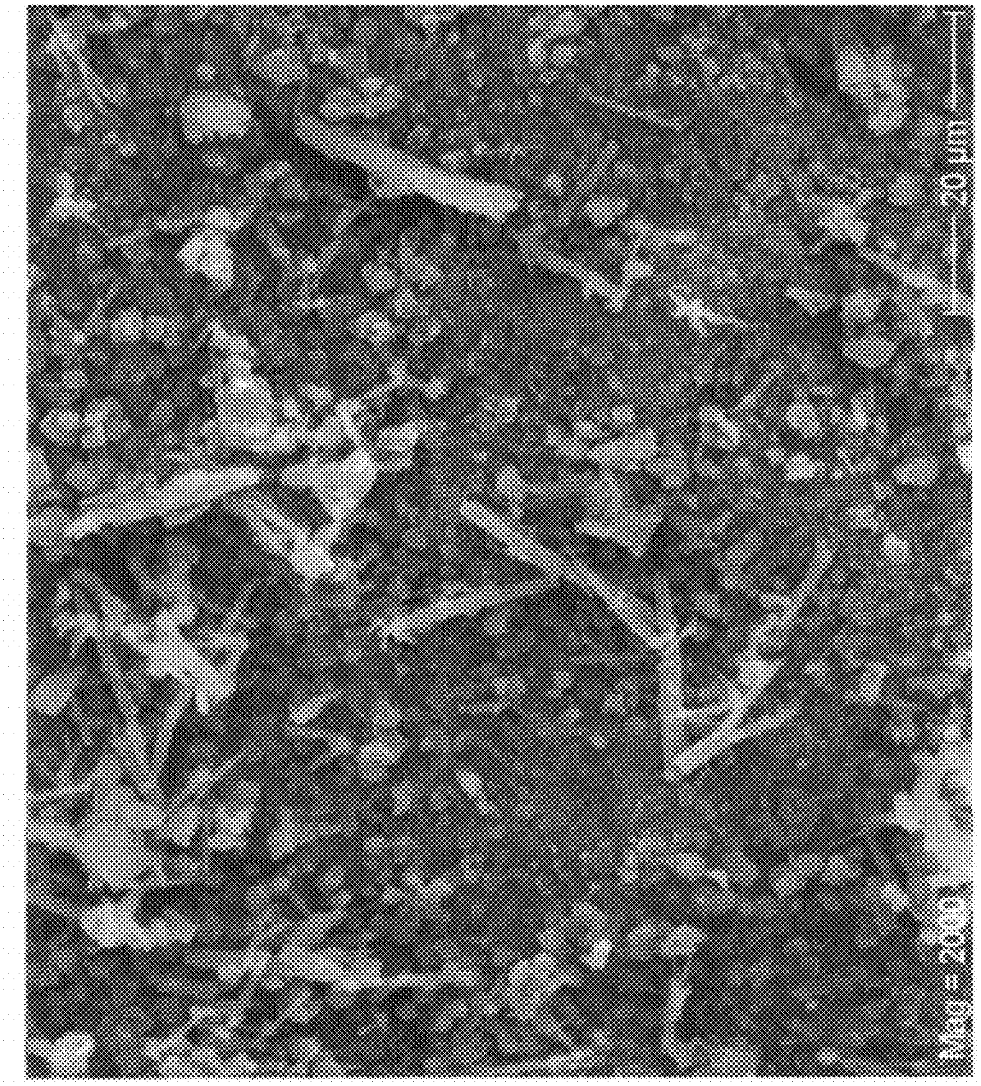
Figure 4A:
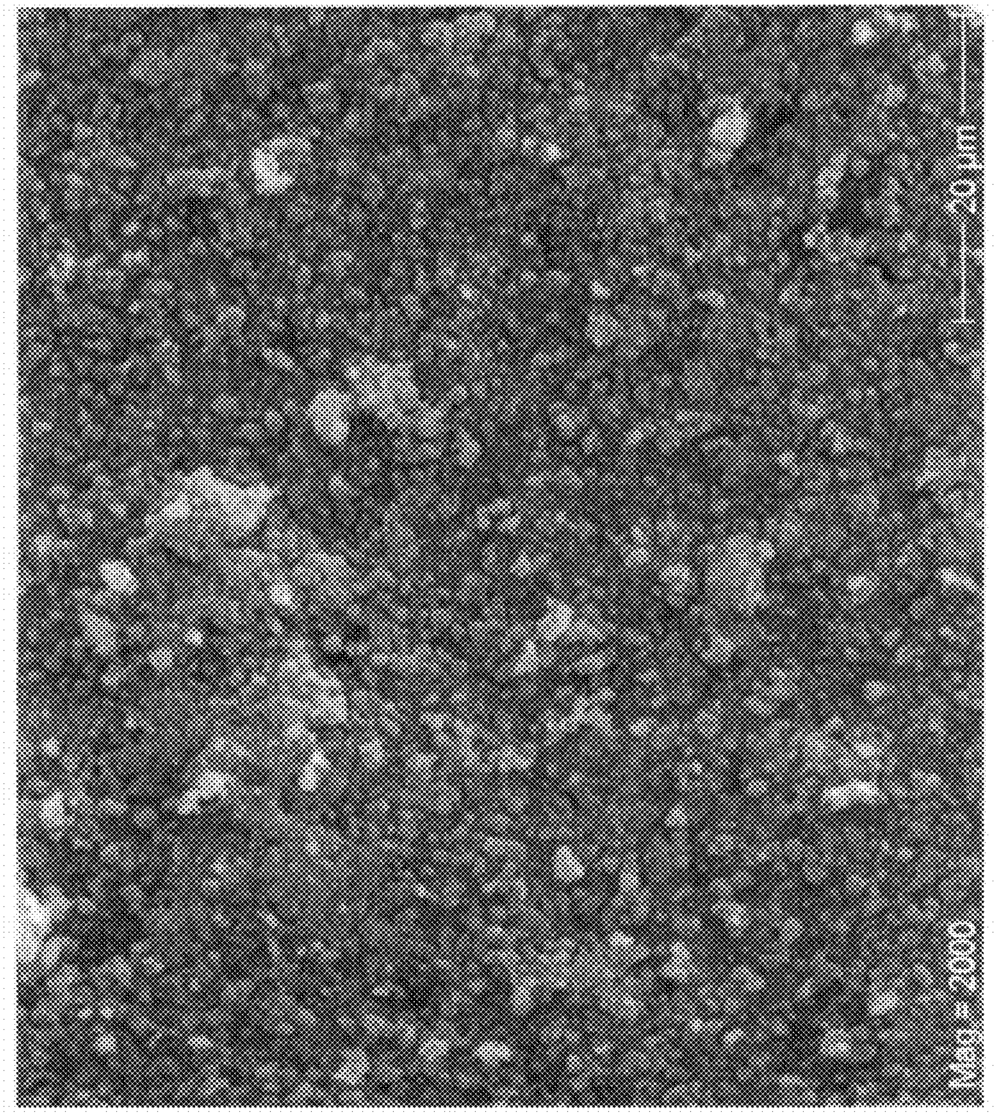
Figure 4B:

Two sets of scanning electron micrograph (SEM) images of HA and carbonated HA are provided, respectively, in FIGS. 3A-B and 4A-B. Reference is made to the elongated inclusions, in random orientation (FIGS. 3B and 4B, respectively), after carbonation of the initial HA material. (FIGS. 3A and 4B, respectively).

Example 9

The strength of a non-porous carbonated apatite material of this invention was tested and compared to non-porous uncarbonated HA using a crush test. The uncarbonated HA sample was sintered at 800° C., and the same temperature was used to sinter the calcium oxide/HA precursor material for the carbonated apatite sample, which was fully converted to a final carbonate content of 15%. Both samples were ground and sieved to a particle size range of 750 to 1000 microns. (It will be understood by those skilled in the art that porous materials of this invention can be prepared using known synthetic techniques and reagents.)

The crush testing was carried out on a Quantrol by Dillon compression test instrument fitted with a 35 pound load cell. The test chamber was a ¼ inch diameter cavity, 2.5 inches deep. The sample to be tested was put in the cavity (1 inch of material) followed by a stainless steel rod that closely fitted the cavity and was used to transmit force from the load cell to the sample. The compression test was carried out at a speed of ⅛ inches/minute, and both force and displacement were measured up to a maximum applied load of 35 pounds.

Figure 5A:
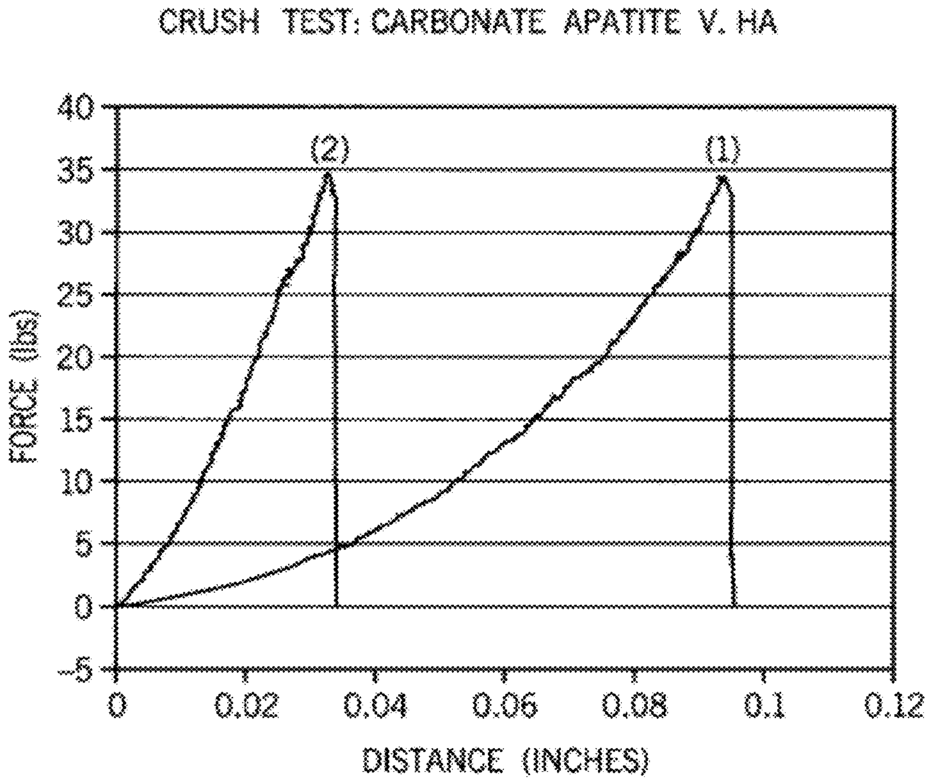
FIGS. 5A-C graphically represent comparative performance test results of an uncarbonated hydroxyapatite sample and representative carbonated hydroxyapatite composites of this invention.
Figure 5B:
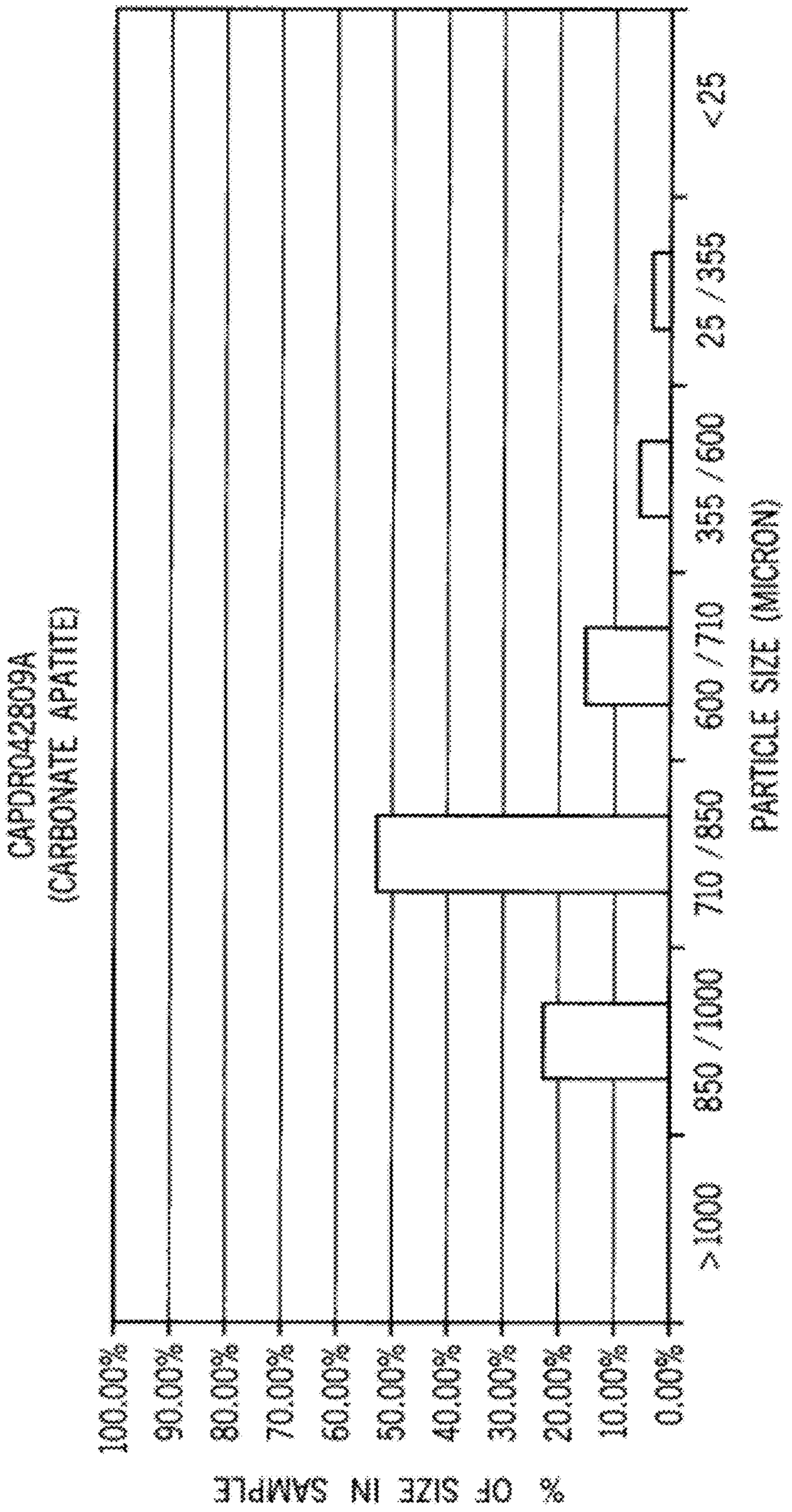
Figure 5C:
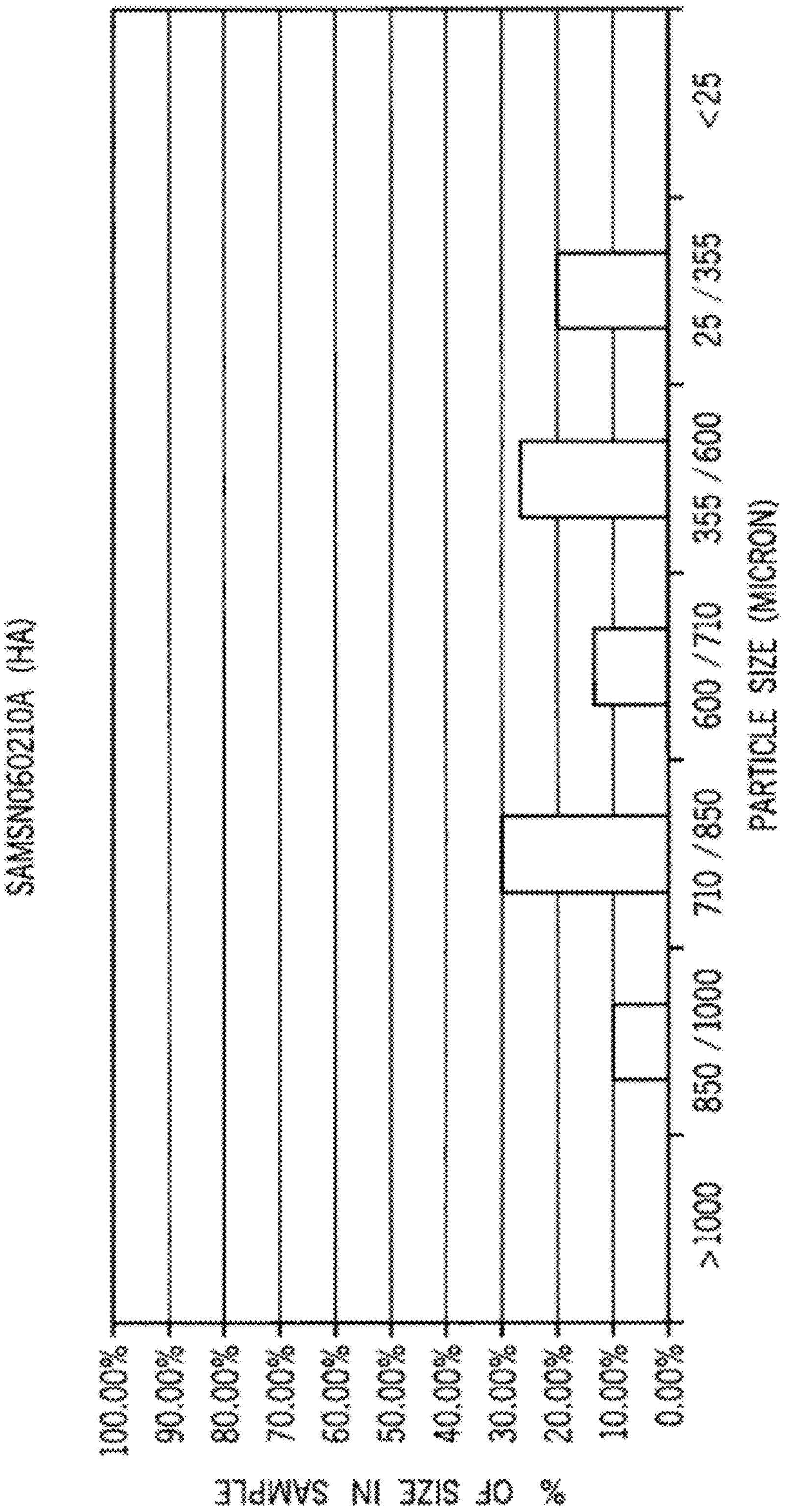

The uncarbonated HA sample was compressed about 0.09 inches, while the carbonated HA sample was compressed about 0.03 inches. (See, FIG. 5A, graphic plots 1 and 2, respectively) Sieve analysis of the materials showed very significant crushing of the HA sample, but little crushing of the carbonated HA sample. About 76% of the carbonated HA sample was still above 710 microns (FIG. 5B), while only about 40% of the HA sample was still above 710 microns (FIG. 5C). Such data clearly demonstrates that a carbonate/HA of this invention has composite physical properties, and is not merely a physical mixture of HA and calcium carbonate. Note, also, that standard sintering temperatures range from about 1100° C.-1200° C., and strength and density increases with sintering temperature. However, contrary to the prior art, enhanced strength was observed here at a much lower sintering temperature (of 800° C.)—thereby avoiding densification of the sort that would otherwise impede resorption.

While the principles of this invention have been described in connection with specific embodiments, it should be understood clearly that these descriptions are added only by way of example and are not intended to limit, in any way, the scope of this invention. For instance, the composites and/or compositions of this invention can be used as or incorporated into various bone grafting or implant materials and/or used as an osteoconductive scaffold for promoting bone growth. Other advantages and features will become apparent from the claims hereinafter, with the scope of such claims determined by the reasonable equivalents, as understood by those skilled in the art.

I claim:

1. A two-phase composite comprising a hydroxyapatite matrix phase and a discontinuous phase within said matrix phase, said composite comprising a Ca/P ratio greater than about 1.67, said discontinuous phase comprising a plurality of elongated, randomly-oriented calcium carbonate inclusions having a length dimension of about 5 microns to about 20 microns, said calcium of said inclusions the excess calcium portion of said Ca/P ratio.

2. The composite of claim 1 wherein at least about 90% of said inclusions have a cross-dimension less than about 10 microns.

3. The composite of claim 1, sintered.

4. The composite of claim 3 comprising a granulated morphology.

5. A composition comprising a two-phase composite comprising a hydroxyapatite matrix phase and a discontinuous phase within said matrix phase, said composite comprising a Ca/P ratio greater than about 1.67, said discontinuous phase comprising a plurality of elongated calcium carbonate inclusions having a length dimension of about 5 microns to about 20 microns, said calcium of said inclusions the excess portion of said Ca/P ratio.

6. The composite of claim 5 comprising a non-powder granulate morphology.

7. The composite of claim 6 comprising granules having a cross-dimension greater than about 100 microns.

* * * * *